United States Patent
Beiriger

(10) Patent No.: US 10,434,299 B2
(45) Date of Patent: Oct. 8, 2019

(54) NON-VENTED VIAL DRUG DELIVERY

(71) Applicant: Fresenius Medical Care Holdings, Inc., Waltham, MA (US)

(72) Inventor: Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 15/957,350

(22) Filed: Apr. 19, 2018

(65) Prior Publication Data
US 2018/0236216 A1    Aug. 23, 2018

Related U.S. Application Data

(62) Division of application No. 14/744,304, filed on Jun. 19, 2015, now Pat. No. 9,974,942.

(51) Int. Cl.
*A61M 1/36* (2006.01)
*A61M 39/24* (2006.01)
(Continued)

(52) U.S. Cl.
CPC ............ *A61M 39/24* (2013.01); *A61M 1/342* (2013.01); *A61M 1/3621* (2013.01);
(Continued)

(58) Field of Classification Search
CPC .. A61M 1/3653; A61M 39/24; A61M 1/3621; A61M 1/342; A61M 5/16831;
(Continued)

(56) References Cited

U.S. PATENT DOCUMENTS 3,946,731 A    3/1976 Lichtenstein
3,982,538 A    9/1976 Sharpe
(Continued)

FOREIGN PATENT DOCUMENTS

DE    4240681    6/1994
DE    102005001779    9/2006
(Continued)

OTHER PUBLICATIONS

Acu-men, Acute Dialysis Machine Operating Instructions, Software Version 1.0, Fresenius MY acumen, Jan. 5, 1996 (OP), 146 pages.
(Continued)

*Primary Examiner* — Amber R Stiles
(74) *Attorney, Agent, or Firm* — Fish & Richardson P.C.

(57) ABSTRACT

This disclosure relates to fluid line sets and related methods. In certain aspects, the fluid line sets include a vial adapter connected to a first end of a fluid line, and a cap removably attached to a second end of the fluid line such that the cap seals the second end of the fluid line. The vial adapter includes a base, a spike extending from a central region of the base, and a sidewall extending from the base and substantially surrounding the spike. The base and the side wall at least partially define a cavity configured to receive a portion of a vial. The cap includes a deformable portion at least partially defining a gas chamber, and the cap is configured so that deformation of the deformable portion causes gas to be forced from the gas chamber to the vial adapter via the fluid line.

10 Claims, 11 Drawing Sheets

(51) Int. Cl.
*A61M 5/14* (2006.01)
*A61M 5/142* (2006.01)
*A61M 5/162* (2006.01)
*A61M 5/168* (2006.01)
*A61M 1/34* (2006.01)
*A61J 1/20* (2006.01)

(52) U.S. Cl.
CPC ...... *A61M 5/1411* (2013.01); *A61M 5/14216* (2013.01); *A61M 5/162* (2013.01); *A61M 5/16831* (2013.01); *A61J 1/201* (2015.05); *A61J 1/2048* (2015.05); *A61M 1/36* (2013.01); *A61M 2205/507* (2013.01)

(58) Field of Classification Search
CPC .......................... A61M 5/162; A61M 5/1411; A61M 5/14216; A61M 1/36; A61M 2205/507; A61J 1/201; A61J 1/2048; A61J 1/22
See application file for complete search history.

(56) References Cited

U.S. PATENT DOCUMENTS

| | | | |
|---|---|---|---|
| 3,985,135 A | 10/1976 | Carpenter et al. |
| 3,996,027 A | 12/1976 | Schnell et al. |
| 4,014,206 A | 3/1977 | Taylor |
| 4,026,669 A | 5/1977 | Leonard et al. |
| 4,137,160 A | 1/1979 | Ebling et al. |
| 4,187,057 A | 2/1980 | Xanthopoulos |
| 4,231,370 A | 11/1980 | Mroz et al. |
| 4,370,983 A | 2/1983 | Lichtenstein |
| 4,459,139 A | 7/1984 | Von Reis et al. |
| 4,488,961 A | 12/1984 | Spencer |
| 4,530,759 A | 7/1985 | Schael |
| 4,572,724 A | 2/1986 | Rosenberg et al. |
| 4,590,227 A | 5/1986 | Nakamura et al. |
| 4,643,713 A | 2/1987 | Vitala |
| 4,662,906 A | 5/1987 | Matkovich et al. |
| 4,695,385 A | 9/1987 | Boag |
| 4,702,675 A | 10/1987 | Aldrovandi et al. |
| 4,702,829 A | 10/1987 | Polaschegg et al. |
| 4,888,004 A | 12/1989 | Williamson |
| 4,898,576 A | 2/1990 | Philip |
| 4,997,464 A | 3/1991 | Kopf |
| 5,061,236 A | 10/1991 | Sutherland et al. |
| 5,330,425 A | 7/1994 | Utterberg |
| 5,425,173 A | 6/1995 | Moss et al. |
| 5,438,510 A | 8/1995 | Bryant et al. |
| 5,441,636 A | 8/1995 | Chevallet et al. |
| 5,460,490 A | 12/1995 | Carr et al. |
| 5,498,338 A | 3/1996 | Kruger |
| 5,540,265 A | 7/1996 | Polaschegg |
| 5,578,070 A | 11/1996 | Utterberg |
| 5,591,344 A | 1/1997 | Kenley et al. |
| 5,614,677 A | 3/1997 | Wamsiedler et al. |
| 5,628,908 A | 5/1997 | Kamen et al. |
| 5,643,205 A | 7/1997 | Utterberg |
| 5,651,893 A | 7/1997 | Kenley et al. |
| 5,674,390 A | 10/1997 | Matthews et al. |
| 5,674,404 A | 10/1997 | Kenley et al. |
| 5,690,831 A | 11/1997 | Kenley et al. |
| 5,693,008 A | 12/1997 | Brugger et al. |
| 5,711,883 A | 1/1998 | Folden et al. |
| 5,714,060 A | 2/1998 | Kenley et al. |
| 5,725,776 A | 3/1998 | Kenley et al. |
| 5,788,671 A | 8/1998 | Johnson |
| 5,849,065 A | 12/1998 | Wojke |
| 5,863,421 A | 1/1999 | Peter et al. |
| 5,928,177 A | 7/1999 | Brugger et al. |
| 5,938,634 A | 8/1999 | Packard |
| 5,989,423 A | 11/1999 | Kamen et al. |
| 6,179,801 B1 | 1/2001 | Holmes et al. |
| 6,196,987 B1 | 3/2001 | Holmes et al. |
| 6,200,287 B1 | 3/2001 | Keller et al. |
| 6,210,591 B1 | 4/2001 | Krivitski |
| 6,231,537 B1 | 5/2001 | Holmes et al. |
| 6,234,989 B1 | 5/2001 | Brierton et al. |
| 6,280,406 B1 | 8/2001 | Dolecek et al. |
| 6,299,583 B1 | 10/2001 | Eggers et al. |
| 6,336,916 B1 | 1/2002 | Bormann et al. |
| 6,337,049 B1 | 1/2002 | Tamari |
| 6,361,518 B1 | 3/2002 | Brierton et al. |
| 6,383,158 B1 | 5/2002 | Utterberg et al. |
| 6,406,631 B1 | 6/2002 | Collins et al. |
| 6,409,696 B1 | 6/2002 | Toavs et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,536,278 B1 | 3/2003 | Scagliarini |
| 6,695,803 B1 | 2/2004 | Robinson et al. |
| 6,725,726 B1 | 4/2004 | Adolfs et al. |
| 6,730,055 B2 | 5/2004 | Bainbridge et al. |
| 6,730,233 B2 | 5/2004 | Pedrazzi |
| 6,743,201 B1 | 6/2004 | Doing et al. |
| 6,755,801 B2 | 6/2004 | Utterberg et al. |
| 6,764,460 B2 | 7/2004 | Dolecek et al. |
| 6,790,195 B2 | 9/2004 | Steele et al. |
| 6,814,864 B1 | 11/2004 | Favre et al. |
| 6,821,441 B2 | 11/2004 | Pedrini et al. |
| 6,852,090 B2 | 2/2005 | Burbank et al. |
| 6,887,214 B1 | 5/2005 | Levin et al. |
| 6,973,373 B2 | 12/2005 | Gray et al. |
| 6,979,309 B2 | 12/2005 | Burbank et al. |
| 7,021,148 B2 | 4/2006 | Kuhn et al. |
| 7,083,596 B2 | 8/2006 | Saied |
| 7,083,719 B2 | 8/2006 | Bowman et al. |
| 7,115,107 B2 | 10/2006 | Delnevo et al. |
| 7,238,164 B2 | 7/2007 | Childers et al. |
| 7,255,680 B1 | 8/2007 | Gharib |
| 7,273,465 B2 | 9/2007 | Ash |
| 7,476,209 B2 | 1/2009 | Gara et al. |
| 7,517,387 B2 | 4/2009 | Chevallet et al. |
| 7,603,907 B2 | 10/2009 | Reiter et al. |
| 7,621,983 B2 | 11/2009 | Neri |
| 7,766,873 B2 | 8/2010 | Moberg et al. |
| 7,871,391 B2 | 1/2011 | Folden et al. |
| 7,892,332 B2 | 2/2011 | Prisco et al. |
| 7,892,331 B2 | 3/2011 | Childers et al. |
| 7,905,853 B2 | 3/2011 | Chapman et al. |
| 8,110,104 B2 | 2/2012 | Crnkovich et al. |
| 2001/0021817 A1 | 9/2001 | Brugger et al. |
| 2002/0014462 A1 | 2/2002 | Muller |
| 2002/0072718 A1 | 6/2002 | Brugger et al. |
| 2002/0123719 A1 | 9/2002 | Lavi |
| 2002/0179527 A1 | 12/2002 | Yao |
| 2004/0019312 A1 | 1/2004 | Childers et al. |
| 2004/0154967 A1 | 8/2004 | Pedrazzi |
| 2004/0238416 A1 | 12/2004 | Burbank et al. |
| 2005/0054968 A1 | 3/2005 | Giannella |
| 2005/0126998 A1 | 6/2005 | Childers |
| 2005/0131332 A1 | 6/2005 | Kelly et al. |
| 2005/0132826 A1 | 6/2005 | Teugels |
| 2005/0230292 A1 | 10/2005 | Beden et al. |
| 2005/0251086 A1 | 11/2005 | Sternby |
| 2005/0274658 A1 | 12/2005 | Rosenbaum et al. |
| 2007/0078369 A1 | 4/2007 | Tamari |
| 2007/0086924 A1 | 4/2007 | Moses |
| 2007/0106198 A1 | 5/2007 | Folden et al. |
| 2007/0112297 A1 | 5/2007 | Plahey et al. |
| 2007/0158247 A1 | 7/2007 | Carr et al. |
| 2007/0158268 A1 | 7/2007 | De Como |
| 2007/0193940 A1 | 8/2007 | Duchamp et al. |
| 2007/0269340 A1 | 11/2007 | Dannenmaier et al. |
| 2008/0149563 A1 | 6/2008 | Ash |
| 2008/0177216 A1 | 7/2008 | Ash |
| 2008/0208011 A1 | 8/2008 | Shuler |
| 2008/0275364 A1 | 11/2008 | Conway |
| 2009/0012442 A9 | 1/2009 | Brugger et al. |
| 2009/0012449 A1 | 1/2009 | Lee et al. |
| 2009/0071911 A1 | 3/2009 | Folden |
| 2009/0084721 A1 | 4/2009 | Yardimci et al. |
| 2009/0101576 A1 | 4/2009 | Rohde et al. |
| 2009/0216211 A1 | 8/2009 | Beden et al. |

(56) References Cited

U.S. PATENT DOCUMENTS

| | | |
|---|---|---|
| 2009/0320684 A1 | 12/2009 | Weaver |
| 2010/0004589 A1 | 1/2010 | Redmann et al. |
| 2010/0063445 A1 | 3/2010 | Sternberg |
| 2010/0133189 A1 | 6/2010 | Maierhofer et al. |
| 2010/0206784 A1 | 8/2010 | Weaver et al. |
| 2010/0222735 A1 | 9/2010 | Plahey et al. |
| 2010/0237011 A1 | 9/2010 | Ross et al. |
| 2010/0292627 A1 | 11/2010 | Caleffi et al. |
| 2011/0120946 A1 | 5/2011 | Levin et al. |
| 2012/0226236 A1* | 9/2012 | Fini ............... A61M 5/155 604/126 |
| 2013/0331635 A1 | 12/2013 | Hoffman et al. |
| 2014/0112828 A1 | 4/2014 | Grant |
| 2014/0230932 A1 | 8/2014 | Fangrow |
| 2015/0083950 A1 | 3/2015 | Okiyama |

FOREIGN PATENT DOCUMENTS

| | | |
|---|---|---|
| EP | 0 235 591 | 9/1987 |
| EP | 0 327 136 | 8/1989 |
| EP | 0458041 | 11/1991 |
| EP | 0728509 | 8/1996 |
| EP | 0887100 | 12/1998 |
| EP | 1529545 | 5/2005 |
| EP | 1547630 | 6/2005 |
| EP | 1728526 | 12/2006 |
| EP | 1894587 | 3/2008 |
| EP | 2 226 087 | 9/2010 |
| GB | 2424966 | 10/2006 |
| JP | 02-289259 | 11/1990 |
| JP | 2002-095741 | 4/2002 |
| JP | 2003-180834 | 7/2003 |
| JP | 2005-218709 | 8/2005 |
| JP | 2005-530543 | 10/2005 |
| WO | WO 96/40322 | 12/1996 |
| WO | WO 9702056 | 1/1997 |
| WO | WO 0108722 | 2/2001 |
| WO | WO 2001/50949 | 7/2001 |
| WO | WO 0164312 | 9/2001 |
| WO | WO 02/026286 | 4/2002 |
| WO | WO 2004/000391 | 12/2003 |
| WO | WO 2005/044340 | 5/2005 |
| WO | WO 2005/044341 | 5/2005 |
| WO | WO 2005/065745 | 7/2005 |
| WO | WO 2005/077490 | 8/2005 |
| WO | WO 2007/050211 | 5/2007 |
| WO | WO 2008/002370 | 1/2008 |
| WO | WO 2010/054345 | 5/2010 |
| WO | WO 2011/002853 | 1/2011 |

OTHER PUBLICATIONS

Dietrich Polaschegg and Levin, Hemodialysis Machines and Monitors, Replacement of Renal Function by Dialysis, Fourth Edition, Chapter 14, pp. 334-379, 1996.

DineshKhullar, Basic Fundamentals of Dialysis, JIMSA, vol. 15, No. 3, pp. 163-169, Jul.-Sep. 2002.

Gambro®, "DEHP-Free Cartridge Blood Sets", © Nov. 2004, Gambro, Inc, Lakewood, CO, 4 pp.

Gambro®, "Prisma® HF 1000, For Increased Filtration Capacity",© Aug. 2001, Gambro Renal Products, Inc., Lakewood, CO, 2 pp.

Gambro®, "Prisma® M60 and M1OO Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex™, Anticipating Critical Care needs and taking our innovative response . . . to new heights", © 2004, Gambro Inc., Lakewood, CO, 8 pp.

Manns et al., "The acu-men: A new device for continuous renal replacement therapy in acute renal failure," Kidney International, vol. 54, pp. 268-274, 1998.

Notification of Transmittal of the International Search Report and the Written Opinion of the International Searching Authority for corresponding PCT Application No. PCT/US2014/043 565, dated Oct. 22, 2014, 13 pages.

Operator's Manual for MeDSpump: A healthy dose of innovation, Fresenius Medical Care North America, 2008, 47 pages.

Wamsiedler et al., Heparin-Free Dialysis with an On-Line Hemodiafiltration System, Artificial Organs, 17(11) pp. 948-953, Feb. 1993.

* cited by examiner

NON-VENTED VIAL DRUG DELIVERY

CROSS REFERENCE RELATED APPLICATION

This application is divisional application of and claims priority to U.S. application Ser. No. 14/744,304, filed on Jun. 19, 2015.

TECHNICAL FIELD

This disclosure relates to non-vented drug delivery.

BACKGROUND

During hemodialysis, impurities and toxins are removed from the blood of a patient by drawing the blood out of the patient through a blood access site, typically via a catheter, and then passing the blood through an artificial kidney (often referred to as a "dialyzer"). The artificial kidney includes microtubes that each separate a first conduit from a second conduit. Generally, a dialysis solution (often referred to as a "dialysate") flows through the first conduit of the dialyzer while the patient's blood flows through the second conduits of the dialyzer, causing impurities and toxins to be transferred from the blood to the dialysate through the microtubes. The impurities and toxins can, for example, be removed from the blood by a diffusion process. After passing through the dialyzer, the purified blood is then returned to the patient.

When kidney failure is diagnosed, patients are typically given medication to help control the symptoms and slow the progress of damage to the kidneys. Patients with chronic kidney failure generally take drugs, such as iron supplements, to control the balance of minerals in the body.

SUMMARY

In one aspect of the invention, a fluid line set includes a vial adapter having a base, a spike extending from a central region of the base, a sidewall extending from the base and substantially surrounding the spike, a fluid line having a first end connected to the vial adapter and a second end, and a cap removably attached to the second end of the fluid line such that the cap seals the second end of the fluid line. The base and the side wall at least partially define a cavity configured to receive a portion of a vial. The cap includes a deformable portion that at least partially defines a gas chamber. The cap is configured so that deformation of the deformable portion causes gas to be forced from the gas chamber to the vial adapter via the fluid line.

In another aspect of the invention, a method includes causing gas to flow through a fluid line of a dialysis system until the gas enters a drug vial connected to a vial adapter assembly causing a pressure within the drug vial to increase, and clamping the fluid line after increasing the drug vial pressure.

In yet another aspect of the invention, a dialysis system includes a dialysis machine including a blood pump and a drug pump, a blood line set including a blood line that can be operably connected to the blood pump and a drip chamber in fluid communication with the blood line, a fluid line set including a fluid line including a first end connected to a vial adapter and a second end, and a cap removably attached to the second end of fluid line such that the cap seals the second end of the fluid line. The cap includes a deformable portion at least partially defining a gas chamber. The cap is configured so that deformation of the deformable portion causes gas to be forced from the gas chamber to the vial adapter via the fluid line.

Implementations can include one or more of the following features.

In some implementations, the cap further includes a one-way valve.

In certain implementations, the one way valve is disposed between the second end of the fluid line and the gas chamber to prevent fluid from passing into the gas chamber from the fluid line.

In some implementations, the chamber includes a volume of sterile gas.

In certain implementations, the sterile gas is air.

In some implementations, the volume of sterile gas includes less than 2 ml of sterile gas.

In certain implementations, the volume of sterile gas includes 1 to 2 ml of sterile gas.

In some implementations, the fluid line includes a first end connected to the vial adapter and a second end and a cap removably attached to the second end of fluid line such that the cap seals the second end of the fluid line. The cap includes a deformable portion at least partially defining a gas chamber. The cap is configured so that deformation of the deformable portion causes gas to be forced from the gas chamber to the vial adapter via the fluid line.

In certain implementations, the method includes fluidly connecting a drug vial with the fluid line via the vial adapter assembly. The vial adapter assembly includes a vial adapter having a spike extending from a central region of a base.

In some implementations, the drug vial includes an initial internal pressure equal to an ambient pressure.

In certain implementations, the drug vial includes an initial gas volume of 0.3 ml to 2 ml.

In some implementations, the gas flowing through the delivery line introduces gas into the drug vial.

In certain implementations, the gas volume within the drug vial is 2 ml to 3 ml.

In some implementations, the introduced gas within the drug vial increases a pressure within the drug vial.

In certain implementations, the method further includes removing the cap from the second end of the fluid line.

In some implementations, the method further includes connecting the second end of the fluid line to an extracorporeal blood circuit.

In some implementations, the method further includes delivering drug from the drug vial to the extracorporeal blood circuit via the drug delivery line.

In certain implementations, the cap further includes a one-way valve.

In some implementations, the one-way valve is disposed between the second end of the fluid line and the gas chamber to prevent fluid from passing into the gas chamber from the fluid line.

In certain implementations, the chamber includes a volume of sterile gas.

In some implementations, the sterile gas is air.

In certain implementations, the volume of sterile gas includes less than 2 ml of sterile gas.

In some implementations, the volume of sterile gas includes 1 to 2 ml of sterile gas.

In some implementations, the dialysis system further includes a drug vial connected to the vial adapter, such that deformation of the deformable portion introduces causes gas to be forced into the drug vial.

In certain implementations, the drug vial includes an initial gas volume of 0.3 to 2 ml.

In some implementations, the additional gas increases the gas volume to 1 to 3 ml.

Implementations can include one or more of the following advantages.

The drug line sets described herein are designed to be used in medical systems, such as hemodialysis systems. Introducing air into the drug vials via the drug line sets of such systems decreases the vacuum pressure within the drug vial, which helps to ensure that the vacuum pressure generated within the drug line set by a pump exceeds the competing vacuum within the drug vial. This additional air improves the process of priming the system by helping to ensure that the desired amount of drug can be withdrawn from the drug vial. In addition, introducing additional air into the drug vial can account for air volume variations between drug vials of different manufacturers or manufacturing lots, which helps to expand the compatibility of the medical devices with a variety of drug vials without modifying any hardware components. Further, by introducing air into the drug vial via the drug delivery line set, both the drug delivery line and the additional air can be sterilized using a single sterilization process.

Other aspects, features, and advantages will be apparent from the description and drawings, and from the claims.

DETAILED DESCRIPTION

Figure 1:
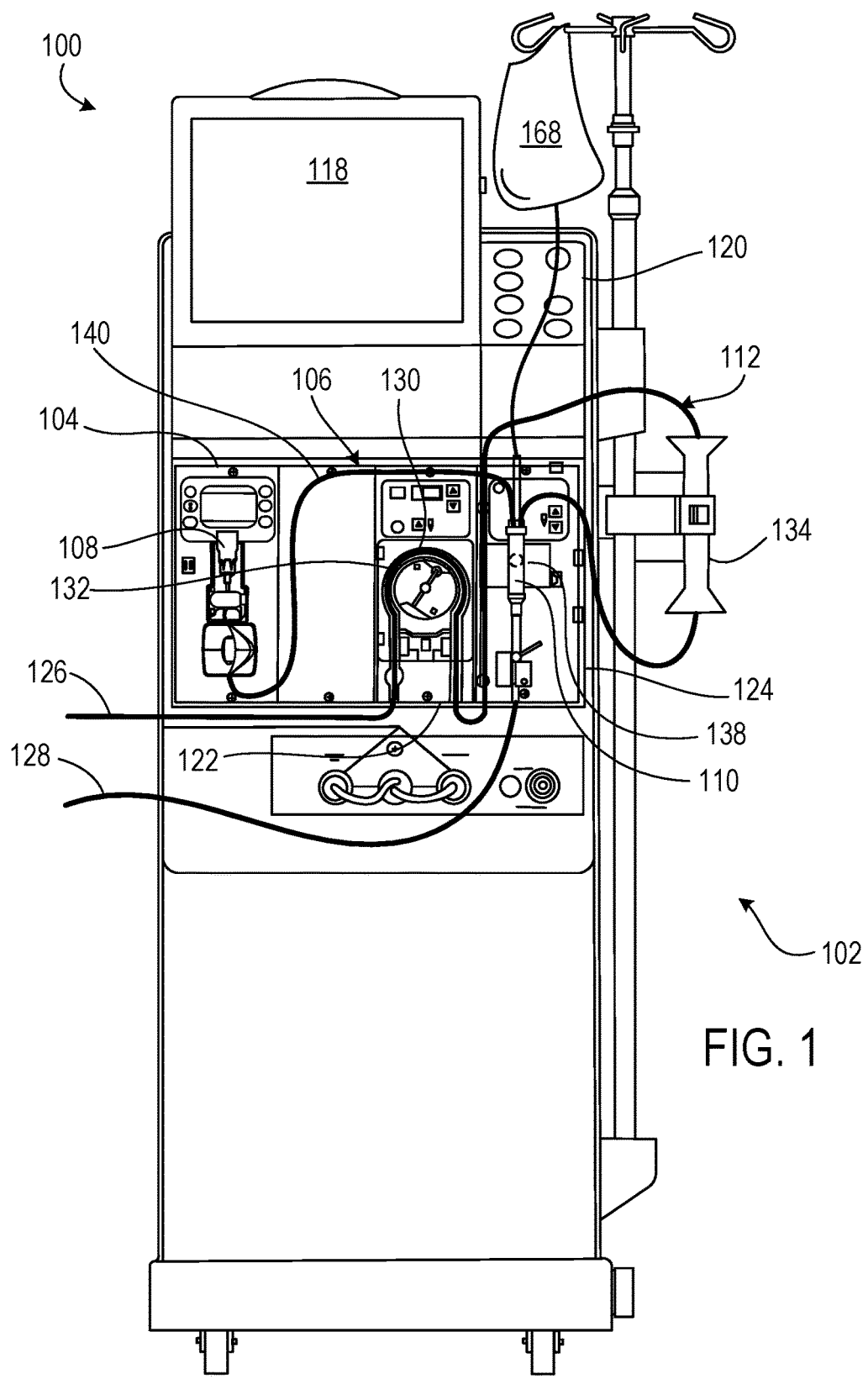
FIG. 1 is a front view of a hemodialysis machine including a drug delivery module mounted in a mid-section of the machine.

Referring to FIG. 1, a hemodialysis system 100 includes a hemodialysis machine 102 having a drug delivery module 104 to which a drug delivery line set 106 is connected. The drug delivery module 104 and the drug delivery line set 106 can be used to deliver one or more drugs to a patient during hemodialysis treatment. Specifically, the drug can be delivered from a drug vial 108 through the drug delivery line set 106 to a drip chamber 110 of a blood line set 112 where the drug mixes with blood before the blood is returned to the patient. As will be described in detail below, a priming cap 116 (shown in FIGS. 3, 4A, 4B, 5, and 11A and 11B) of the drug delivery line set 106 includes a diaphragm that can introduce air into the drug vial 108 using a drug delivery line 140 of the drug delivery line set 106. Introducing air into the drug vial 108 modifies the internal pressure within the drug vial 108 to ensure that the vacuum pressure within the drug delivery line 140, throughout treatment, exceeds the competing vacuum within the drug vial 108.

Still referring to FIG. 1, the hemodialysis machine 102 includes a display 118 and a control panel 120, whereby the user selections and instructions can be sent to, and stored by, a control unit of the hemodialysis machine 102. The hemodialysis machine 102 also includes modules that house components used to perform hemodialysis, including the drug delivery module 104, a blood pump module 122, and a level detector module 124.

In use, the disposable blood line set 112, which forms a blood circuit with the patient, is connected to the modules 104, 122, and 124 on the front side of the hemodialysis machine 102. During treatment, patient lines 126, 128 of the blood line set 112 are connected to the patient, and a pump tubing segment 130 of the blood line set 112 is connected to a blood pump 132 of the blood pump module 122. As the blood pump 132 is operated, blood is drawn from the patient, pumped through a dialyzer 134 and the drip chamber 110 of the blood line set 112, and then returned to the patient.

Figure 2:
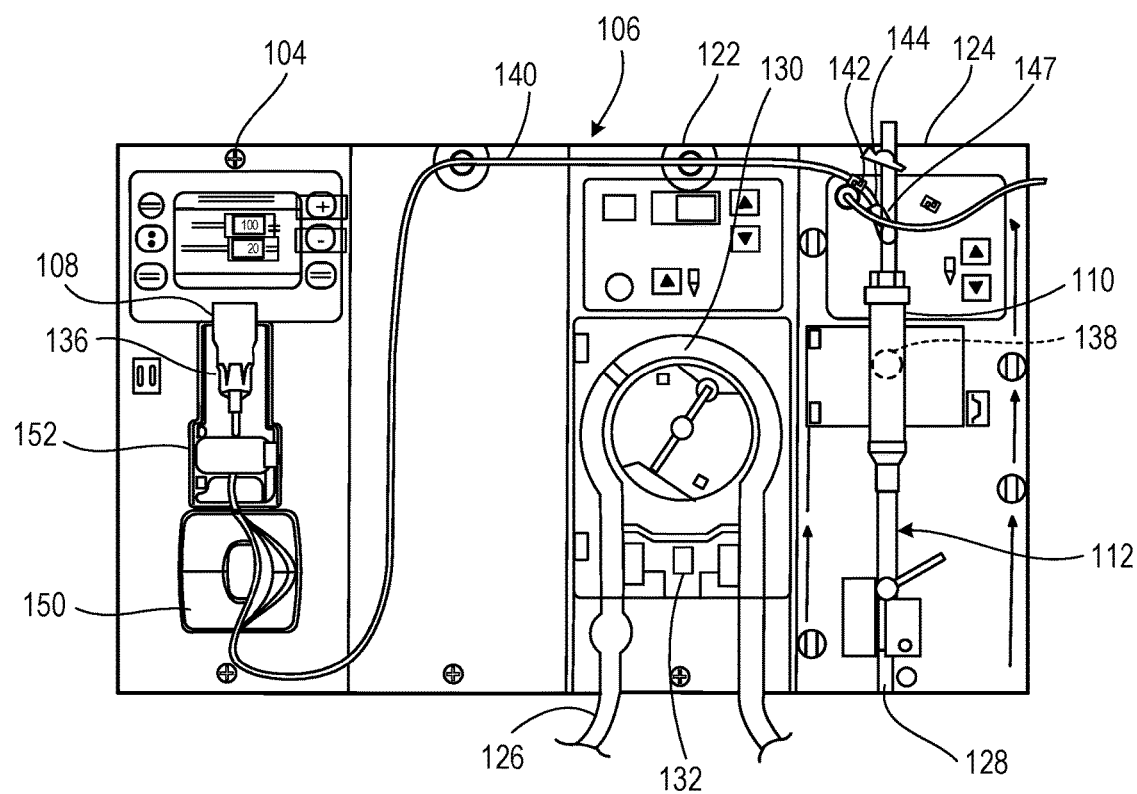
FIG. 2 is an enlarged view of the midsection of the hemodialysis machine of FIG. 1.

FIG. 2 illustrates the mid-section of the hemodialysis machine 102 with the blood line set 112 and the drug delivery line set 106 connected to the modules 104, 122, and 124 and with the drug vial 108 inserted into a vial adapter 136 of the drug delivery line set 106. The blood line set 112 includes the pump tubing segment 130, which is connected to the blood pump module 122 in a manner so as to operatively engage the blood pump 132 of the blood pump module 122. Operation of the blood pump 132 pumps blood through the blood line set 112.

Still referring to FIG. 2, the drip chamber 110 of the blood line set 112 is positioned at a location downstream from the blood pump 132. The drip chamber 110 permits gas, such as air, in the blood to escape from the blood before the blood is returned to a patient. The drip chamber 110 can be secured to the level detector module 124 so as to align with a fluid level detector 138 that is adapted to detect the level of liquid (e.g., blood and/or saline) within the drip chamber 110. The drug delivery line 140 of the drug delivery line set 106 is connected to the blood line set 112 at a location between the dialyzer 134 and the drip chamber 110 via a luer lock connector 142 disposed on the drug delivery line 140. Specifically, the luer lock connector 142 is connected to a mating luer locking fitting on a level adjust line 144 that is connected to the top of the drip chamber 110. A clamp 147 is attached to the level adjust line 144 and is used to permit or block fluid from passing between the drug delivery line set 106 and the blood line set 112.

The drug delivery line set 106 includes the drug delivery line 140, which is connected to the drug delivery module 104 in a manner so as to operatively engage the drug pump 150 of the drug delivery module 104. When the drug pump 150 is being operated, a vacuum pressure (e.g., up to about −12 psi) is applied to the drug vial 108 that is connected to the drug delivery line 140. In certain cases, the initial pressure in the drug vial 108 can vary slightly from above to below ambient pressure due to variations in conditions during manufacturing. The initial air volume within the drug vial 108 is generally 2 ml of air or less (e.g., from about 0.40 ml to 1.75 ml of air) due to drug vial arrangements (e.g., total interior volume, ambient pressure during vial filling, and stopper volume), and when all of the drug has been delivered, the ending pressure within the vial is −15 psi or less (e.g., −7 to −15 psi). As the quantity of drug in the drug vial decreases, a vacuum (or negative pressure) within the drug vial increases because the drug vial 108 is not vented. In other words, the pressure within the drug vial 108 progresses from 14.7 psi toward −15 psi (e.g., −7, −7.22, −8, −13, −13.6 psi) as the drug is being delivered. In certain cases, the vacuum generated in the drug delivery line 140 exceeds the vacuum within the drug vial 108. As a result, the drug is drawn from the drug vial 108 through the drug delivery line 140. However, when the pump 150 is unable to generate a vacuum in the drug delivery line 140 that exceeds the vacuum in the drug vial, the pump 150 can no longer draw drug from the drug vial 108 into the drug delivery line 140. Thus, any remaining drug within the drug vial 108 is not delivered to the patient. The remaining drug can result in under-delivery of a drug to the patient and/or limit the amount of available drug per drug vial.

Figure 3:
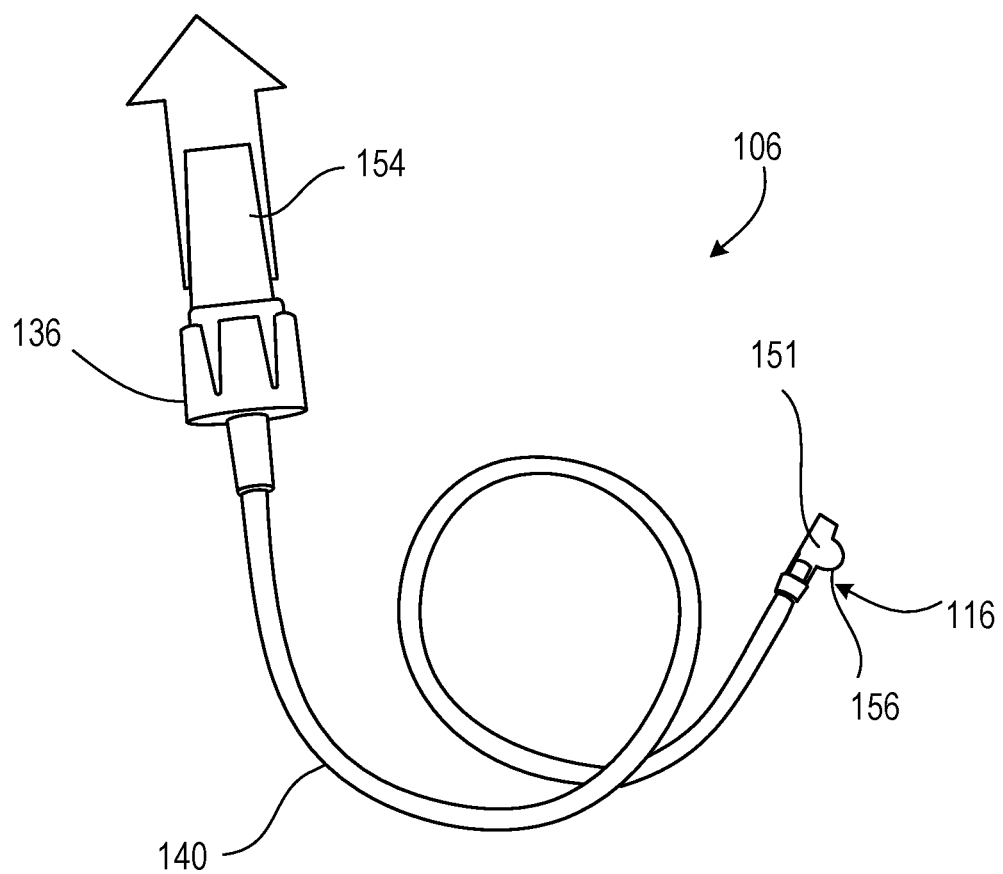
FIG. 3 is a perspective view of a drug delivery fluid line set including a vial spiking assembly and priming cap connected to a drug delivery line.

As shown in FIG. 3, the drug delivery line set 106 includes the vial adapter 136 to which the drug delivery line 140 is attached. The drug delivery line set 106 also includes a priming cap 116 that is removably attached to the drug delivery line 140. The drug delivery line 140 and the priming cap 116 include sterile air. The priming cap 116 includes a bistable diaphragm 156, which defines a top boundary of an internal chamber 151. The air volume can be selected such that, upon activation of the priming cap 116, the bistable diaphragm 156 displaces a sufficient air volume into a drug vial (e.g., the drug vial 108) to enable a pump (e.g., the drug pump 150) to deliver the desired dosage or substantially all of the drug (e.g., 100%, at least 95%, at least 90%, or at least 80%) within the drug vial based on the capabilities of the pump. For example, the internal chamber 151 can be sized and shaped to store an air volume of about 3 ml or less (e.g., 0.5 ml or less, 1 ml or less, 1.5 ml or less, or 2 ml or less), which can be delivered into a drug vial (e.g., the drug vial 108) through the drug delivery line 140 when the priming cap 116 is activated.

In addition to the priming cap 116, the drug delivery line set 106 can include a spike cover 154 is removably secured to the vial adapter 136 by an interference fit. The spike cover 154 can be made of a moldable material, e.g. polyethylene. The spike cover 154 is removed from the vial adapter 136 prior to use to allow a drug vial (e.g., the drug vial 108) to be inserted into the vial adapter 136.

Figure 4A:
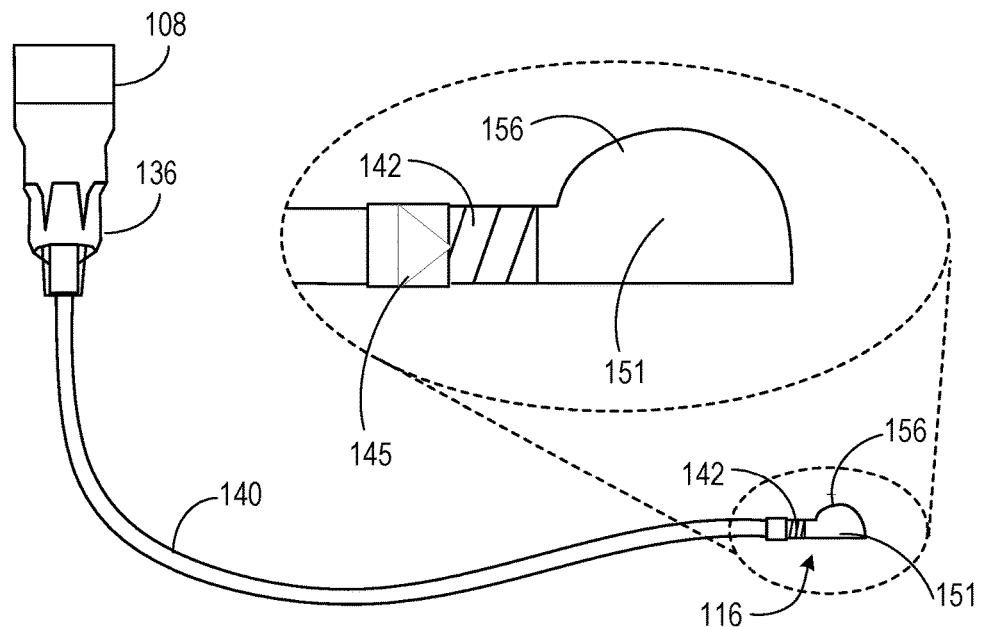
FIG. 4A is a perspective view of the drug delivery line set including the priming cap in the unactuated state and an enlarged view of the priming cap in an unactuated state.
Figure 4B:
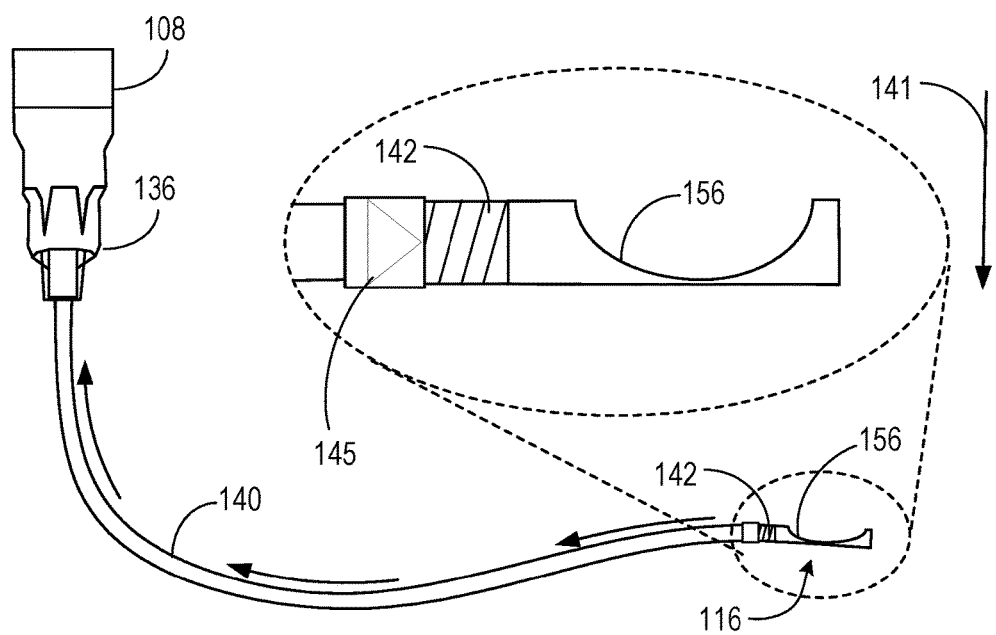
FIG. 4B is a perspective view of the drug delivery line set including the priming cap in the actuated state and an enlarged view of the priming cap in an actuated state.

FIGS. 4A and 4B illustrate the drug delivery line set 106 with the drug vial 108 inserted into the vial adapter 136. The bistable diaphragm 156 is movable between a first position in which the bistable diaphragm 156 assumes a convex shape (as shown in FIG. 4A) and a second position in which the bistable diaphragm assumes a concave shape (as shown in FIG. 4B). For example, the bistable diaphragm 156 is convex prior to being depressed in the direction shown by an arrow 141 and is concave after the priming cap 116 is depressed. Activation of the priming cap 116 is achieved by depressing the convex surface to create a concave surface.

The priming cap 116 can be made from a plastic material (e.g. high density Polyethylene (HDPE), polyethylene, polyvinylchloride, polyamide, or a blend of moldable plastics). The bistable diaphragm 156 can be economically produced using an injection molding technique, for example. The priming cap 116 removably attaches to the drug line 140 using a luer connection to form an air-tight seal with the fluid line 140. Other air-tight connection mechanisms may also be used (an interference fit).

The drug delivery line set 106 also includes a one-way valve 145 (e.g., a check valve) between the luer lock connector 142 of the drug delivery line set 106 and the drug vial 108. The one-way valve 145 permits delivery of air from the internal chamber 151 to the drug vial 108, but prevents air from re-entering the priming cap 116 when the bistable diaphragm 156 is deformed and/or released. The one-way valve 145 may be a duckbill valve, an umbrella valve, a ball-check valve, diaphragm check valve, swing check valve, stop-check valve, lift-check valve or a combination thereof.

As drug is delivered from the drug vial 108, any remaining air within the drug vial 108 expands and a vacuum pressure within the drug vial 108 increases. The final pressure within the drug vial can be determined with the following equations:

$$P_{atm}(V_{initial\ air}) = P_{vial}(V_{min.\ air})$$ Equation 1 Minimum Final Vial Pressure $$P_{atm}(V_{initial\ air}) = P_{vial}(V_{max.\ air})$$ Equation 2 Maximum Final Vial Pressure where $P_{atm}$ is atmospheric pressure.

$V_{initial\ air}$ is the initial volume of air inside the vial;

$P_{vial}$ is the final pressure within the vial; and $V_{max}$ is maximum volume of air inside the vial.

By subtracting the pressure within the drug delivery line 140 (e.g., ambient pressure or 14.7 psi) from the calculated final vial pressure, the pumping capability necessary to evacuate all drug can be determined. The initial volume of air inside the vial can be adjusted such that pump (e.g., the drug pump 150) can generate a vacuum (based on the capabilities of the pump) in the drug line that exceeds final vacuum within the drug vial in view of the maximum and minimum conditions given arrangement of a drug vial (e.g., the total vial volume, the air volume, the drug volume, and the stopper volume). This adjustment helps to ensure that the medical systems described herein remain compatible with a variety of drug vial designs and/or manufacturing deviations without replacing or upgrading system components (e.g., pumps).

Figure 5:
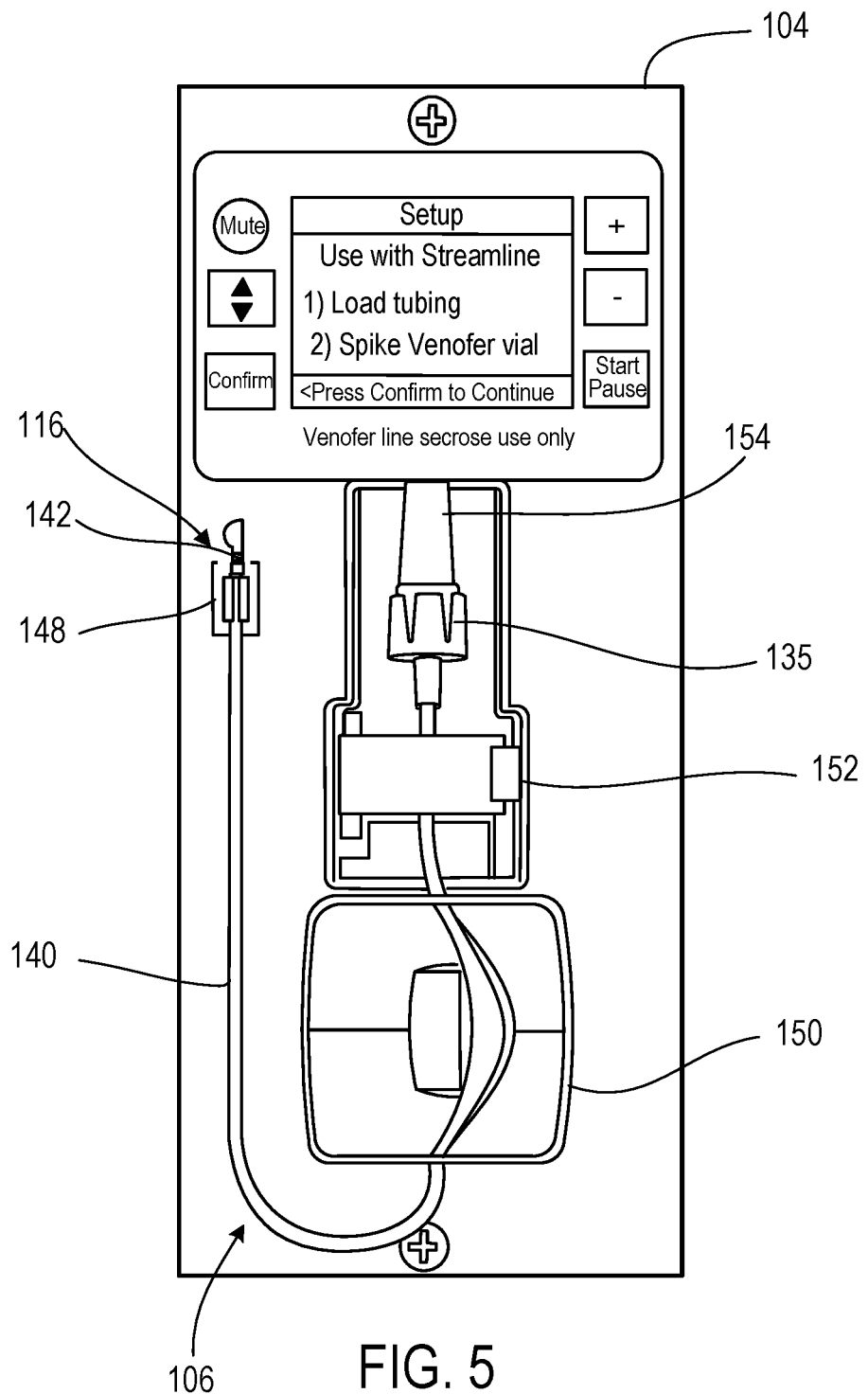
FIG. 5 is an enlarged view of the drug delivery module of the hemodialysis machine of FIG. 1 isolated from the hemodialysis machine.

FIG. 5 shows the drug delivery line set 106 connected to the drug delivery module 104 prior to connecting the drug delivery line 140 to the blood line set 112. As shown, the end of the drug delivery line 140 is connected to a storage clip 148 of the drug delivery module 104. The drug delivery line 140 passes through a peristaltic drug pump 150. Prior to use, a user will prime the drug vial 108 with air by depressing the priming cap 116, which will be explained in further detail later. A user then would unclip the drug delivery line 140 from the storage clip 148 and connect it to the blood line set 112 in the manner shown in FIGS. 1 and 2.

Still referring to FIG. 5, the drug delivery module 104 includes a fluid flow detector 152. The fluid flow detector 152 is capable of detecting air bubbles within the drug delivery line 140. As a result, the fluid flow detector 152 can determine whether the drug vial 108 is empty. In some implementations, the fluid flow detector 152 is an optical detector. The OPB 350 level detector made by Optek® can, for example, be used. Other types of optical detectors can alternatively or additionally be used. Similarly, other types of sensors, such as sensors utilizing ultrasound technology can be used as the fluid flow detector. Examples of such sensors include the AD8/AD9 Integral Ultrasonic Air-In- Line, Air Bubble Detector and the BD8/BD9 Integral Ultrasonic Air Bubble, Air-In-Line & Liquid Level Detection Sensors (manufactured by Introtek® International (Edgewood, N.Y.)). In some implementations, the fluid flow detector 152 includes a sensor that, in addition to sensing the presence of an air bubble within its associated drug delivery line 140, can sense the presence of the drug delivery line 140 itself.

Still referring to FIG. 5, the drug delivery line 140 passes through (e.g., is threaded through) the peristaltic drug pump 150. The peristaltic drug pump 150 works by compressing the drug delivery line 140 and moving a "pillow" of fluid that is pinched between two points of the drug delivery line 140 by the pump rollers. Each "pillow" of fluid is of a volume determined by the roller spacing and the inside diameter of the drug delivery line 140. When the peristaltic drug pump 150 operates at a given speed, a series of these "pillow" shaped volumes of fluid are delivered to the drip chamber 110. The rate of fluid delivery can be changed by altering the speed of the peristaltic drug pump 150. The pump speed can be controlled, for example, by adjusting the voltage delivered to the peristaltic drug pump 150. The voltage delivered to the motor of the peristaltic drug pump 150 can, for example, be adjusted by the control unit (e.g., software of the control unit) until the correct speed (e.g., the speed that corresponds to the desired flow rate) is measured by an encoder of the peristaltic drug pump 150.

During use, the drug delivery line set 106 is fluidly connected to the blood line set 112 of the hemodialysis system 100, as shown in FIGS. 1 and 2. Drugs are delivered to the drip chamber 110 using the drug delivery module 104. The drugs mix with the patient's blood within the drip chamber 110 and are then delivered to the patient along with the patient's filtered blood.

Figure 6:
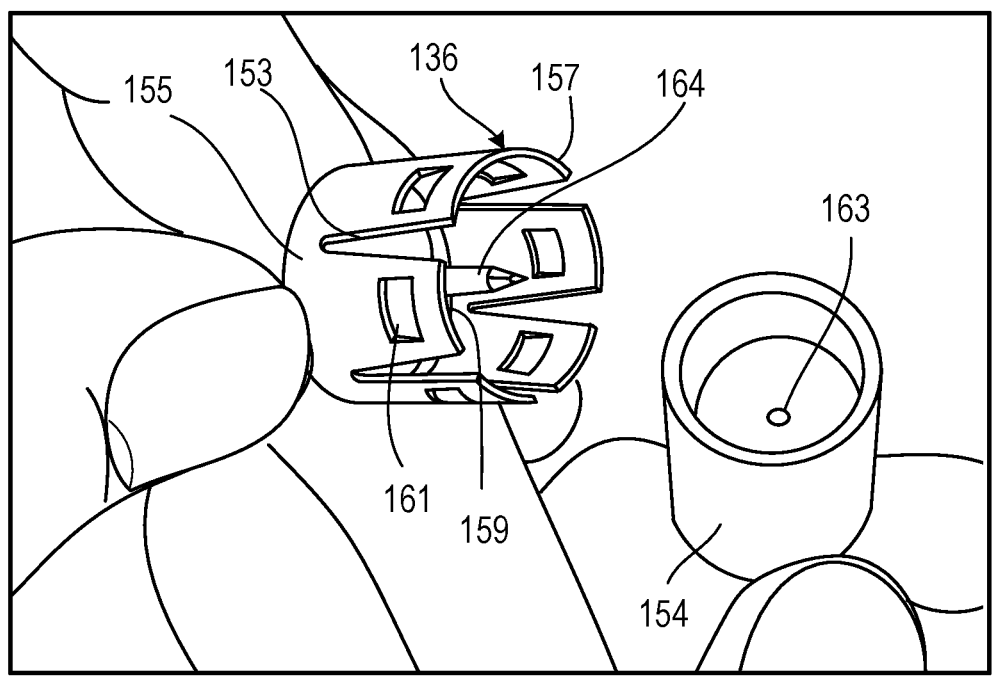
FIG. 6 is a perspective view of the vial spiking assembly and a spike cover.

FIG. 6 illustrates the vial adapter assembly with the spike cover 154 removed from the vial adapter 136. The vial adapter 136 includes circumferentially spaced side wall segments 157 that extend upwardly from a base 155 to form a receiving cavity 159 sized and shaped to receive a drug vial. A spike 164 extends from a central region of the base 155 and is sized and shaped to pierce a seal of the drug vial when the drug vial is inserted into the receiving cavity 159. The spike 164 has a central passage in fluid communication with a cavity 163 of the spike cover 154 when the spike cover 154 is positioned over the spike 164.

As shown in FIG. 6, the circumferential side wall segments 157 of the vial adapter 136 extend to a slightly greater height than the spike 164 of the vial adapter 136. Adjacent side wall segments 157 are spaced apart by longitudinal/vertical slots 153. The side wall segments 157 together with the base 155 form the receiving cavity 159 that is configured to receive a portion of a drug vial (e.g., a collar of a drug vial cap assembly). In some implementations, the receiving cavity 159 is configured to receive a collar having a diameter that is about 0.75 inches to about 1 inch (e.g., about 0.875 inches.) The side wall segments 157 are configured to deflect away from the longitudinal axis of the vial adapter 136 when a radially outward force is applied (e.g., as a result of the drug vial being inserted into the receiving cavity 159) and rebound towards the longitudinal axis when the force is released.

Still referring to FIG. 6, protrusions 161 on side wall segments 157 of the vial adapter 136 help secure a vial within the receiving cavity 159 of the vial adapter 136. The extension of the side wall segments 157 to a slightly greater height that the spike 164 of the vial adapter 136 also help to ensure that the spike 164 is not inadvertently contacted (e.g., by the user) prior to loading of the drug vial 108 onto the spike 164. This can, for example, help to prevent the spike 164 from becoming contaminated before it is inserted into the drug vial.

In some implementations, the spike 164 is formed of one or more medical grade plastics, such as PVC or acrylonitrile butadiene styrene (ABS). However, other medical grade plastics can be used to form the spike 164. Similarly, certain metals, such as stainless steel, could be used to form the spike 164.

Another feature of the vial adapter assembly that prevents inadvertent contact and contamination is the spike cover 154. The spike cover 154 is placed into the receiving cavity 159 of the vial adapter 136 to cover the spike 164. The spike cover 154 can help prevent objects from contacting and contaminating the spike 164 prior to use and can also prevent users from inadvertently sticking themselves with the spike 164. The spike cover 154 is configured to be received in the receiving cavity 159 and temporarily retained by the side wall segments 157. For example, the spike cover 154 can be retained via a loose interference fit. The side wall segments 157 provide a resisting force of about 0.75 lbf to about 2 lbf to retain the spike cover 154 when it is retained by the vial adapter 136.

Prior to hemodialysis, the user connects the drug delivery line set 106, which includes the vial adapter 136, the spike cover 154, and the drug delivery line 140, to the drug delivery module 104 of the hemodialysis machine 102. The drug delivery line set 106 is typically provided to the user in a sterile bag with the priming cap 116 connected to the end of the drug delivery line 140 opposite the vial adapter 136. To connect the drug delivery line set 106 to the drug delivery module 104, the user first opens the sterile bag and removes the drug delivery line set 106.

Figure 7:
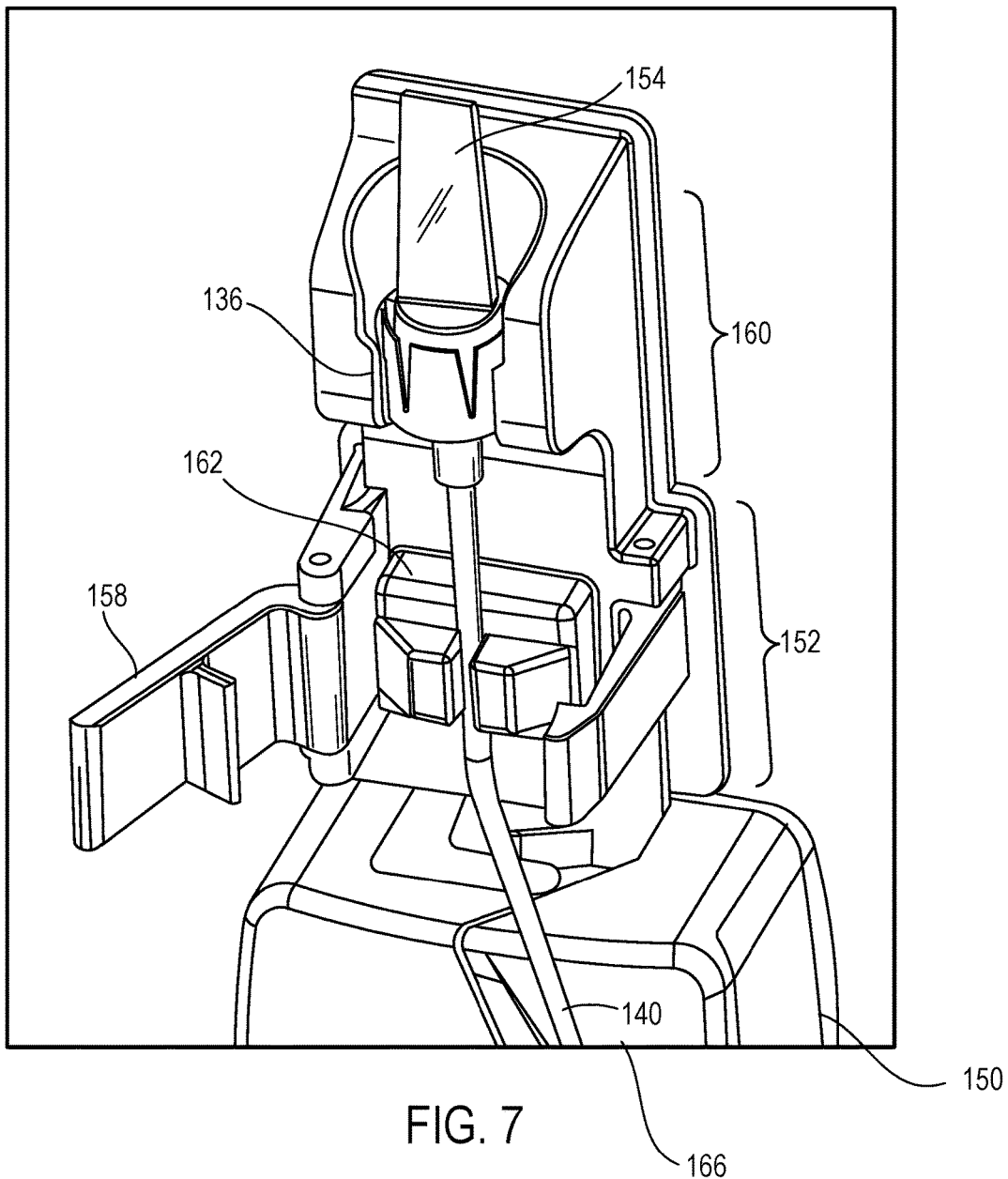
FIG. 7 is a perspective view of the drug delivery line set partially loaded into the drug delivery module.

Referring to FIG. 7, the user then opens a door 158 of the fluid flow detector 152, places the vial adapter assembly (e.g., the vial adapter 136 and spike cover 154) into a vial holder 160, and threads the drug delivery line 140 through a bubble detector 162 of the fluid flow detector 152. The user also opens a door 166 of the peristaltic drug pump 150 and threads the drug delivery line 140 through the peristaltic drug pump 150. The door 166 typically remains open so that the drug delivery line 140 is not crimped between the door 166 and the rollers of the peristaltic drug pump 150. This permits both fluid and air to flow freely through the drug delivery line 140.

Figure 8:
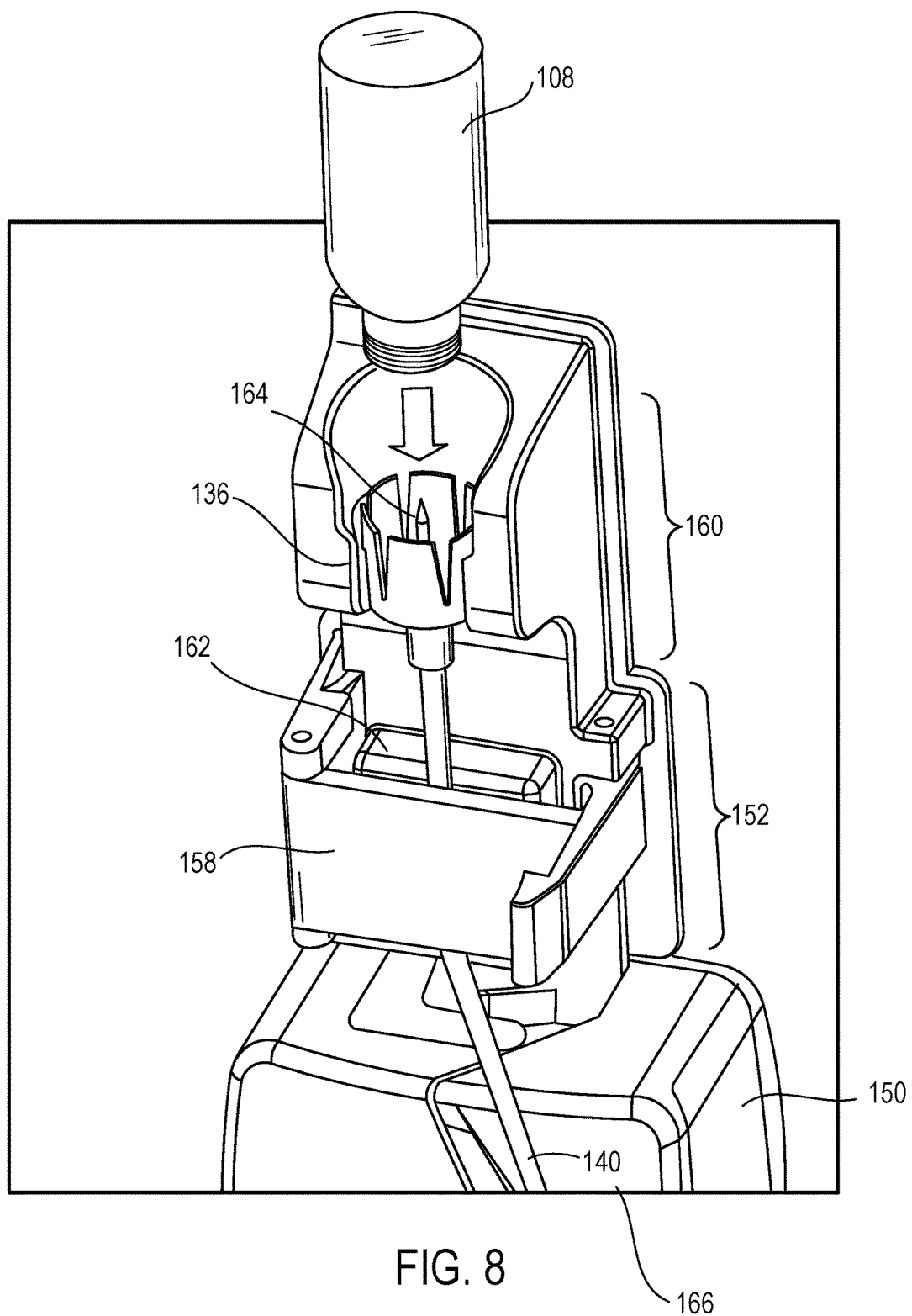
FIG. 8 is a perspective view of the drug vial being loaded onto the vial adapter.

Referring to FIG. 8, the drug vial 108 is placed on the vial adapter 136 so that a spike 164 pierces a seal of the drug vial 108 and places the vial in fluid connection with the drug delivery line set 106 (e.g., as shown in FIGS. 1 and 2). When placed on the vial adapter 136, the seal and the spike 164 form a fluid- and air-tight seal. A user then depresses and/or deforms the priming cap 116 (as shown in FIG. 4B) to deliver air into the drug vial 108.

Figure 9:
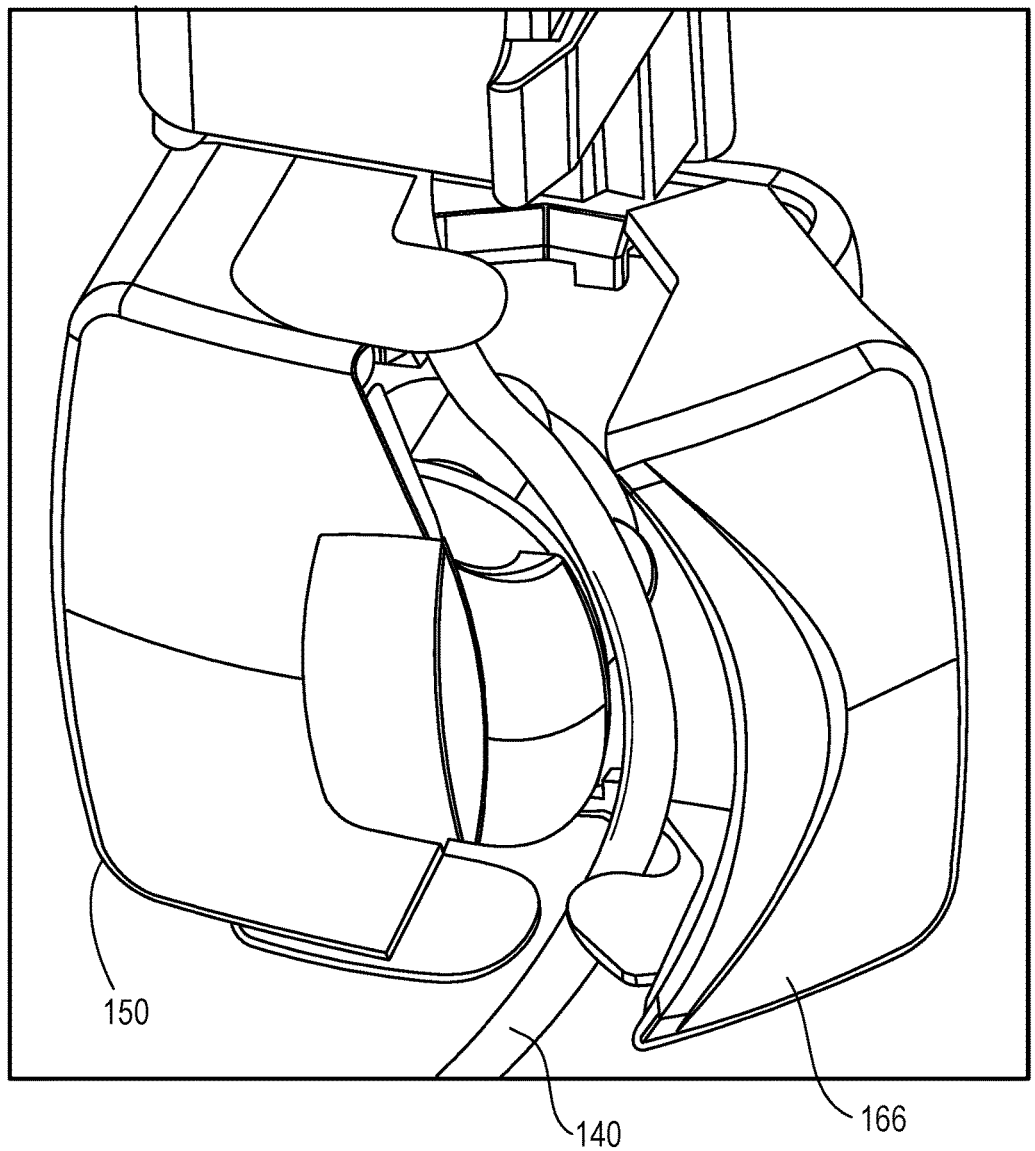
FIG. 9 is a perspective view of the drug delivery line set being loaded into a peristaltic pump of the drug delivery module.

Referring to FIG. 9, the user then closes the door 166 of the peristaltic drug pump 150 and the door 158 of the fluid flow detector 152, engaging the peristaltic drug pump 150 and the fluid flow detector 152 with the drug delivery line 140. As discussed above, the drug delivery line 140 is crimped within the door 166. This arrangement helps to retain the modified drug vial pressure and/or the additional air when, for example, a priming cap is removed and/or the drug line is fluidly connected to another line because portions of the drug line 140 downstream from the door 166 may equalize with another pressure, e.g., with the pressure within the blood line set.

Figure 10:
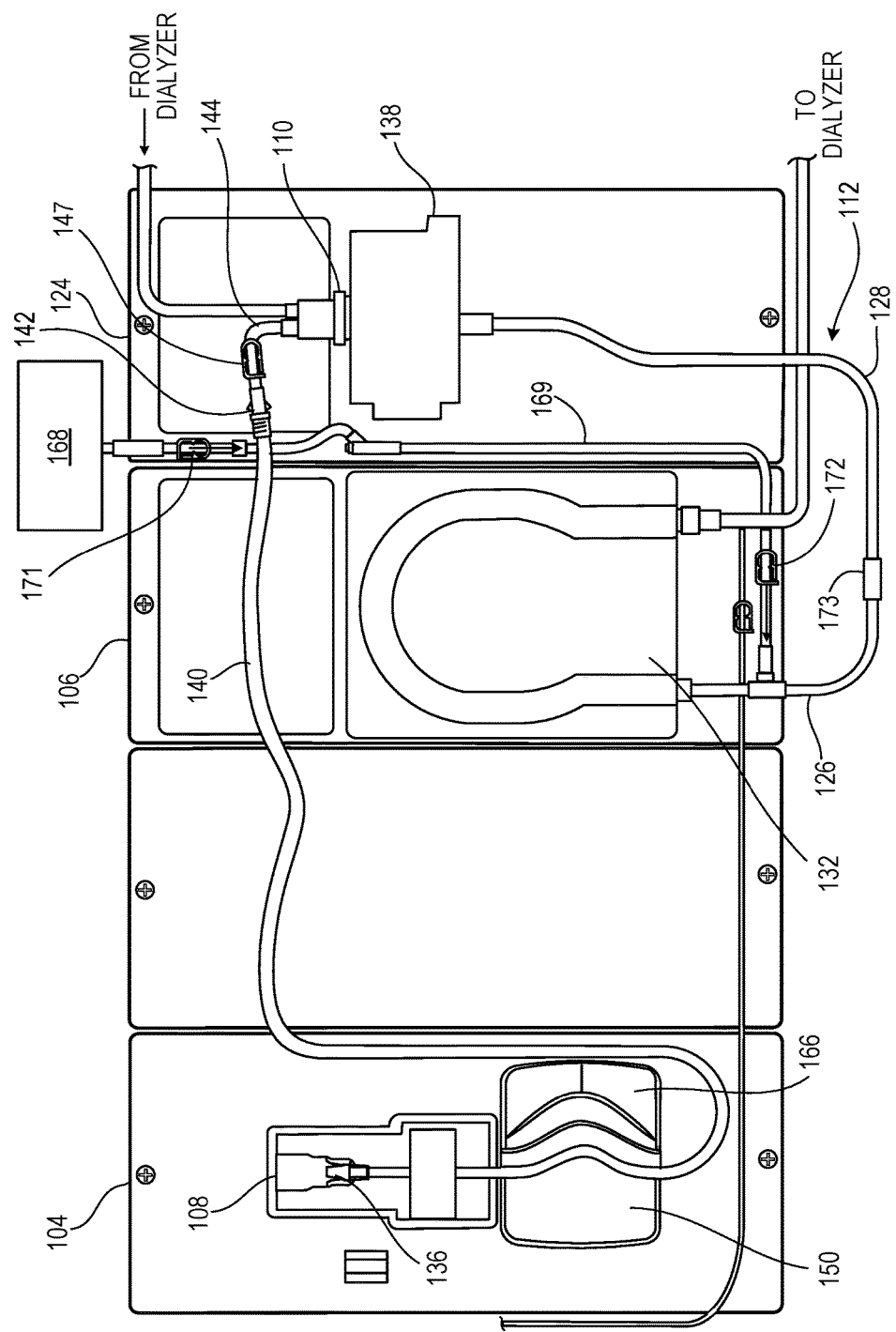
FIG. 10 is an enlarged view of the midsection of the hemodialysis machine of FIG. 1 showing the drug delivery line set connected to the hemodialysis set prior to operating the pumps. Certain details of the hemodialysis machine have been omitted for simplicity.

Referring to FIG. 10, the drug delivery line 140 is then connected to the drip chamber 110 using an aseptic technique. As discussed above, this typically involves removing the priming cap 116 and connecting the luer lock connector 142 on the end of the drug delivery line 140 to a mating luer lock fitting on the level adjust line 144 extending from the drip chamber 110. In addition, a priming fluid bag 168 is connected to the blood line set 112 via a priming fluid line 169. The priming fluid bag 168 is connected to the priming fluid line 169 by a luer lock connection. The priming fluid line 169 also includes clamps 171 and 172 that are used to regulate the fluid flow from the priming fluid bag 168 to the blood line set 112. The patient lines 126 and 128 are connected to each other via a luer connector 173 at this point to allow priming fluid to circulate through the blood circuit.

Still referring to FIG. 10, after the drug delivery line set 106 has been connected to the drip chamber 110, which is attached to the level detector module 124, the peristaltic drug pump 150 is then operated to deliver drug to the drip chamber 110 of the blood line set 112. For example, the system can undergo a priming process in which the drug pump 150 causes a portion of the drug to be drawn from the drug vial 108 until the drug is detected by the bubble detector 162. The blood pump 132 is also operated to cycle priming fluid through the blood line set 112 and through the dialyzer 134. Air within the blood circuit and drug delivery line can collect in the drip chamber 110 and then be removed from the system prior to treatment.

After priming is complete, the priming fluid line 169 is disconnected from the blood circuit or clamped, and the patient lines 126 and 128 are disconnected from each other and connected to the patient to allow the patient's blood to circulate through the blood circuit. During treatment, the peristaltic blood pump 132 is operated to pull blood from the patient via the arterial patient line 126, run the blood through the blood circuit, and then return the blood to the patient via the venous patient line 128. The drug pump 150 is operated to deliver drug from the drug vial 108 to the drip chamber 110 through the drug delivery line 140. The drug can mix with the blood in the drip chamber 110 before flowing to the patient.

As discussed above, the drip chamber 110 of the hemodialysis system 100 functions as an air trap. Thus, any gases (e.g., air) introduced into the system are able to escape from the drug and blood within the drip chamber 110 before the mixture of blood and drug is delivered to the patient. In addition to removing air from the system, the drip chamber 110 provides other benefits. For example, the drip chamber 110 provides visual confirmation of drug delivery and allows the delivered drug to mix with the patient's blood prior to reaching the patient. In addition, the drip chamber 110 allows for simple luer connection to the drug delivery line set 106. As a result, the patient need not be stuck with an additional needle in order to receive the drug from the drug vial 108.

While certain embodiments have been described, other embodiments are possible.

While the priming cap 116 has generally been shown and described as monolithic, the priming cap 116 can be a composite structure where the bistable diaphragm 156 is an attachable component that could be a different material from the main body of the priming cap. The bistable diaphragm 156 can be attached to the main body of the priming cap with any attachment known in the art, such as adhesives, fasteners, or welding.

Figure 11A:
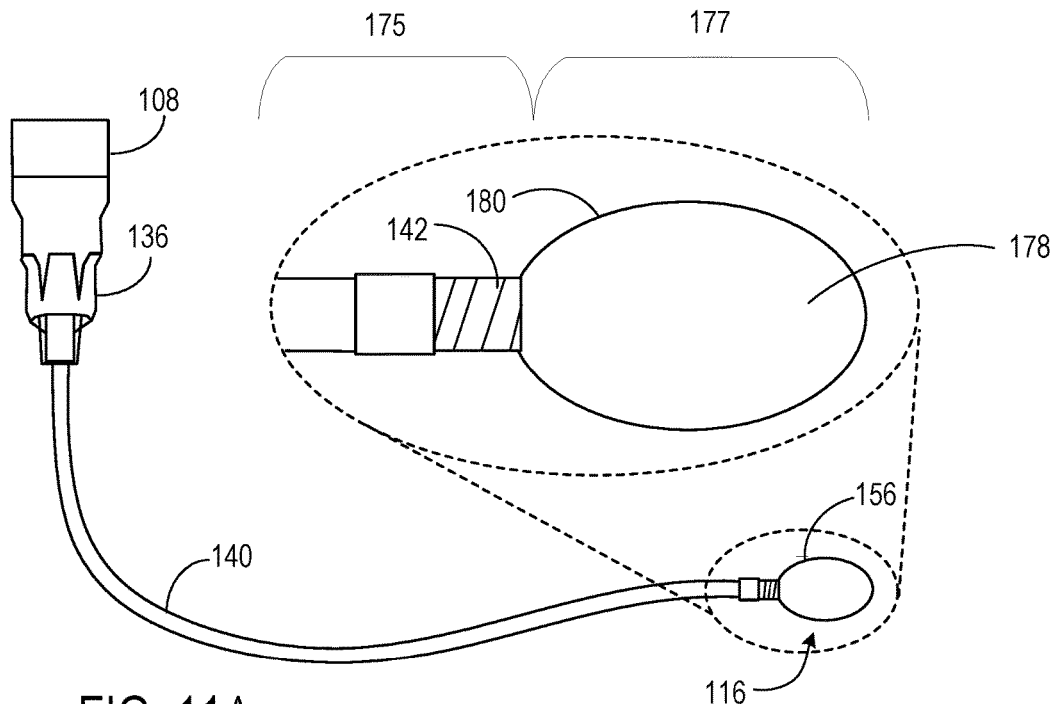
FIGS. 11A and 11B are a perspective views of an alternative priming cap in the form of a dropper.
Figure 11B:
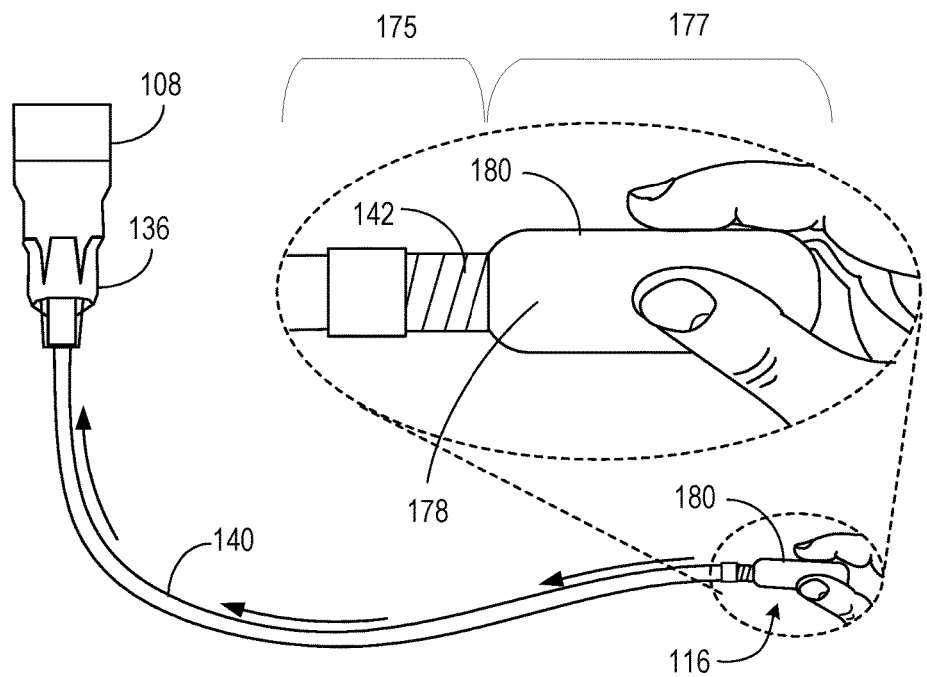

Referring to FIGS. 11A and 11B, while the priming cap 116 has been generally shown as having an asymmetric body partially defined by the bistable diaphragm 156, the priming cap 116 can alternatively or additionally have a uniform compressible body such that any portion of the priming cap can be compressed to introduce air to the drug vial 108. For example, the priming cap can include a compressible body portion 177 (e.g., a bulbous portion) surrounding an internal gas chamber 178 in fluid communication (e.g., via an internal passage) with an integral neck portion 175 extending from the compressible body portion 177. The compressible body portion 177 can alternatively or additionally have a uniform shape. For example, the compressible body portion 177 can be arranged as an elliptical cylinder with at least one spherical end (as shown in FIG. 11A) or as a cylinder with at least one spherical end (as shown in FIG. 11B). The integral neck portion 175 can include a fluid-tight (e.g., air-tight) connection (as described with above) to removably connect the priming cap 116 to the fluid line. Compressing the body portion 177 can deform a portion of the deformable wall structure 180, thereby reducing the volume of the internal gas chamber 178 and expelling at least a portion of gas (e.g., air and/or sterile air) from the interior gas chamber 1758. The deformable wall structure 180 defines at least a top surface and a bottom surface of the internal gas chamber 178. This arrangement provides multiple surfaces for a user to deform and/or compress to deliver gas to the drug vial 108 via the drug line 140.

While the diaphragm has been described as being bistable, in some embodiments, it can have a single stable state. The user continuously depresses the diaphragm in order to maintain the additional air displaced into the drug vial. The user can control the amount of air delivered based on the amount of pressure the user places on the diaphragm. The user can connect the drug delivery line set to the drip chamber while depressing the diaphragm.

While the priming cap 116 has generally been shown to include a one way-valve, in some embodiments, the priming cap can additionally or alternatively be arranged to occlude the drug delivery line 140 via depression of the bistable diaphragm 156, thereby preventing air from re-entering the priming cap 116. Upon depression and/or deformation, the bistable diaphragm 156 can contact an opposing wall surface to form a fluid-tight seal until the cap is removed.

While a luer lock connection has been described as being used to fluidly connect the drug delivery line set with the priming cap 116 and the drip chamber, any of various other types of fluid connections can be implemented, such as an interference fit, tab connection, or temporary adhesive.

While during priming the drug vial the drug delivery line is generally shown as threaded through the peristaltic drug pump, the drug delivery line may remain outside of the peristaltic pump before the priming cap 116 is removed. For example, a user can deform or depress the priming cap 116 before threading the drug delivery line through the peristaltic drug pump (e.g., over the pump rollers).

While the hemodialysis machine has generally been shown to include modules used to perform hemodialysis, including the drug delivery module, the blood pump module, and the level detector module, other modules may also be included. For example, a heparin pump module may also be included. The heparin pump module can include a heparin pump that receives a syringe connected to a drug delivery line that is connected to the blood line at a location between the blood pump. The syringe pump can be operated to move a plunger of the syringe and thus eject liquid from the syringe through the drug delivery line. The heparin pump module can thus be used to inject heparin from the syringe into the blood circuit via the drug delivery line during a hemodialysis treatment.

While the drug delivery devices have been described as being used with hemodialysis systems, the devices, assemblies, and methods described herein can be used with various other types of drug delivery processes and systems. For example, in some implementations, the drug vial spiking devices are used for delivering drugs during peritoneal dialysis treatments, blood perfusion treatments, intravenous infusion treatments, or other medical fluid handling treatments, such as delivering drugs intravenously.

A number of implementations have been described. Nevertheless, it will be understood that various modifications may be made without departing from the spirit and scope of the description. Accordingly, other implementations are within the scope of the following claims.

What is claimed is:

1. A method comprising:
    causing a gas to flow through a fluid line of a dialysis system until the gas enters a drug vial connected to a vial adapter assembly causing a pressure within the drug vial to increase; and
    clamping the fluid line after increasing the drug vial pressure,
    wherein the fluid line comprises a first end connected to the vial adapter assembly and a second end, and a cap removably attached to the second end of fluid line such that the cap seals the second end of the fluid line, the cap comprising: a deformable portion at least partially defining a gas chamber, the deformable portion being a bistable diaphragm configured to be activated by depression so that deformation of the deformable portion causes gas to be forced from the gas chamber to the vial adapter assembly via the fluid line.

2. The method of claim 1, further comprising fluidly connecting a drug vial with the fluid line via the vial adapter assembly, the vial adapter assembly comprising a vial adapter having a spike extending from a central region of a base.

3. The method of claim 2, wherein the drug vial includes an initial internal pressure equal to an ambient pressure.

4. The method of claim 3, wherein the drug vial includes an initial gas volume of 0.3 ml to 2 ml.

5. The method of claim 2, wherein the gas flowing through a delivery line introduces gas into the drug vial.

6. The method of claim 5, wherein the introduced gas volume within the drug vial is 1 ml to 2 ml.

7. The method of claim 5, wherein the introduced gas within the drug vial increases a pressure within the drug vial.

8. The method of claim 1, further comprising removing the cap from the second end of the fluid line.

9. The method of claim 8, further comprising connecting the second end of the fluid line to an extracorporeal blood circuit.

10. The method of claim 9, further comprising delivering drug from the drug vial to the extracorporeal blood circuit via a drug delivery line.

* * * * *

UNITED STATES PATENT AND TRADEMARK OFFICE
CERTIFICATE OF CORRECTION

| | | |
|---|---|---|
| PATENT NO. | : 10,434,299 B2 | Page 1 of 1 |
| APPLICATION NO. | : 15/957350 | |
| DATED | : October 8, 2019 | |
| INVENTOR(S) | : Michael James Beiriger | |

It is certified that error appears in the above-identified patent and that said Letters Patent is hereby corrected as shown below:

In the Specification

Column 1, Line 5, after "is" insert --a--.

Signed and Sealed this
Thirty-first Day of December, 2019

Andrei Iancu
*Director of the United States Patent and Trademark Office*